United States Patent
Lalleman et al.

(10) Patent No.: US 9,375,393 B2
(45) Date of Patent: Jun. 28, 2016

(54) COMPOSITION COMPRISING A NON-NITROGENOUS ZINC SALT AND A PARTICULAR CATIONIC SURFACTANT

(75) Inventors: Boris Lalleman, Paris (FR); Estelle Mathonneau, Paris (FR); Julie Brun, Asnieres-sur-Seine (FR)

(73) Assignee: L'OREAL, Paris (FR)

( * ) Notice: Subject to any disclaimer, the term of this patent is extended or adjusted under 35 U.S.C. 154(b) by 0 days.

(21) Appl. No.: 13/996,067

(22) PCT Filed: Dec. 19, 2011

(86) PCT No.: PCT/EP2011/073296
§ 371 (c)(1),
(2), (4) Date: Sep. 16, 2013

(87) PCT Pub. No.: WO2012/084866
PCT Pub. Date: Jun. 28, 2012

(65) Prior Publication Data
US 2013/0340784 A1    Dec. 26, 2013

Related U.S. Application Data

(60) Provisional application No. 61/431,621, filed on Jan. 11, 2011.

(30) Foreign Application Priority Data

Dec. 21, 2010 (FR) .................................... 10 60954

(51) Int. Cl.
| | |
|---|---|
| *A61Q 5/00* | (2006.01) |
| *A61K 8/58* | (2006.01) |
| *A61K 8/20* | (2006.01) |
| *A61K 8/23* | (2006.01) |
| *A61K 8/27* | (2006.01) |
| *A61K 8/365* | (2006.01) |
| *A61K 8/368* | (2006.01) |
| *A61K 8/41* | (2006.01) |
| *A61K 8/45* | (2006.01) |
| *A61K 8/46* | (2006.01) |
| *A61Q 5/12* | (2006.01) |

(52) U.S. Cl.
CPC ... *A61K 8/58* (2013.01); *A61K 8/20* (2013.01); *A61K 8/23* (2013.01); *A61K 8/27* (2013.01); *A61K 8/365* (2013.01); *A61K 8/368* (2013.01); *A61K 8/416* (2013.01); *A61K 8/45* (2013.01); *A61K 8/466* (2013.01); *A61Q 5/004* (2013.01); *A61Q 5/12* (2013.01)

(58) Field of Classification Search
CPC ............. A61Q 5/12; A61K 8/20; A61K 8/27; A61K 8/368; A61K 8/466; A61K 8/45
USPC .......................... 424/70.1, 70.4, 70.27, 70.28
See application file for complete search history.

(56) References Cited

U.S. PATENT DOCUMENTS

| | | |
|---|---|---|
| 2,261,002 A | 10/1941 | Ritter |
| 2,271,378 A | 1/1942 | Searle |
| 2,273,780 A | 2/1942 | Dittmar |
| 2,375,853 A | 5/1945 | Kirby et al. |
| 2,388,614 A | 11/1945 | Kirby et al. |
| 2,454,547 A | 11/1948 | Bock et al. |
| 2,961,347 A | 11/1960 | Floyd |
| 3,206,462 A | 9/1965 | McCarty |
| 3,227,615 A | 1/1966 | Korden |
| 3,472,840 A | 10/1969 | Stone et al. |
| 3,632,559 A | 1/1972 | Matter et al. |
| 3,874,870 A | 4/1975 | Green et al. |
| 3,910,862 A | 10/1975 | Barabas et al. |
| 3,912,808 A | 10/1975 | Sokol |
| 3,917,817 A | 11/1975 | Vanlerberghe et al. |
| 3,929,990 A | 12/1975 | Green et al. |
| 3,966,904 A | 6/1976 | Green et al. |
| 3,986,825 A | 10/1976 | Sokol |
| 4,001,432 A | 1/1977 | Green et al. |
| 4,005,193 A | 1/1977 | Green et al. |
| 4,013,787 A | 3/1977 | Varlerberghe et al. |
| 4,017,460 A | 4/1977 | Tessler |
| 4,025,617 A | 5/1977 | Green et al. |
| 4,025,627 A | 5/1977 | Green et al. |

(Continued)

FOREIGN PATENT DOCUMENTS

| | | |
|---|---|---|
| EP | 0 080 976 A1 | 6/1983 |
| EP | 0 095 238 A2 | 11/1983 |

(Continued)

OTHER PUBLICATIONS

English abstract of the Patent EP 2198837 A1.*
International Search Report for PCT/EP2011/073296.
PCT/IB/308 Form for PCT/FR2011/052988.
English Language Abstract for EP 0 080 976. (1983).
Non-Final Office Action dated Nov. 4, 2013 cited in co-pending U.S. Appl. No. 13/995,984.
Co-pending U.S. Appl. No. 13/995,984; National Stage of International Application No. PCT/EP2011/073345; Geraldine Fack et al., "Cosmetic Composition Comprising a Particular Zinc Salt and a Starch," filed Jun. 20, 2013.
International Search Report for PCT/EP2011/073345.
English language abstract for EP 1051967 (Nov. 15, 2000).
English language abstract for EP 1776983 (Apr. 25, 2007).
English language abstract for FR 2944967 (Nov. 5, 2010).

*Primary Examiner* — Eisa Elhilo
(74) *Attorney, Agent, or Firm* — The Marbury Law Group, PLLC

(57) ABSTRACT

Composition comprising a non-nitrogenous zinc salt and a particular cationic surfactant The present invention relates to a cosmetic composition comprising, in a cosmetically acceptable medium, at least one particular zinc salt and at least one cationic surfactant chosen from particular quaternary ammonium salts, in a specific weight ratio. Another subject of the invention relates to a process for treating keratin fibers, using such a composition, and to the use of such a composition, preferably in the form of a leave-on care product, for conditioning keratin fibers and protecting their artificial color from fading.

20 Claims, No Drawings

(56) References Cited

U.S. PATENT DOCUMENTS

| | | |
|---|---|---|
| 4,025,653 A | 5/1977 | Green et al. |
| 4,026,945 A | 5/1977 | Green et al. |
| 4,027,008 A | 5/1977 | Sokol |
| 4,027,020 A | 5/1977 | Green et al. |
| 4,075,136 A | 2/1978 | Schaper |
| 4,137,180 A | 1/1979 | Naik et al. |
| 4,157,388 A | 6/1979 | Christiansen |
| 4,165,367 A | 8/1979 | Chakrabarti |
| 4,172,887 A | 10/1979 | Vanlerberghe et al. |
| 4,185,087 A | 1/1980 | Morlino |
| 4,189,468 A | 2/1980 | Vanlerberghe et al. |
| 4,197,865 A | 4/1980 | Jacquet et al. |
| 4,217,914 A | 8/1980 | Jacquet et al. |
| 4,223,009 A | 9/1980 | Chakrabarti |
| 4,240,450 A | 12/1980 | Grollier et al. |
| 4,277,581 A | 7/1981 | Vanlerberghe et al. |
| 4,348,202 A | 9/1982 | Grollier et al. |
| 4,349,532 A | 9/1982 | Vanlerberghe et al. |
| 4,381,919 A | 5/1983 | Jacquet et al. |
| 4,390,689 A | 6/1983 | Jacquet et al. |
| 4,422,853 A | 12/1983 | Jacquet et al. |
| 4,445,521 A | 5/1984 | Grollier et al. |
| 4,579,732 A | 4/1986 | Grollier et al. |
| 4,608,250 A | 8/1986 | Jacquet et al. |
| 4,652,445 A | 3/1987 | Ort |
| 4,702,906 A | 10/1987 | Jacquet et al. |
| 4,719,099 A | 1/1988 | Grollier et al. |
| 4,719,282 A | 1/1988 | Nadolsky et al. |
| 4,777,040 A | 10/1988 | Grollier et al. |
| 4,839,166 A | 6/1989 | Grollier et al. |
| 4,874,554 A | 10/1989 | Lange et al. |
| 4,948,579 A | 8/1990 | Jacquet et al. |
| 4,970,066 A | 11/1990 | Grollier et al. |
| 4,996,059 A | 2/1991 | Grollier et al. |
| 5,009,880 A | 4/1991 | Grollier et al. |
| 5,089,252 A | 2/1992 | Grollier et al. |
| 5,196,189 A | 3/1993 | Jacquet et al. |
| 5,374,334 A | 12/1994 | Sommese et al. |
| 5,455,340 A | 10/1995 | Bernard et al. |
| 5,681,554 A | 10/1997 | Cannell et al. |
| 5,958,392 A | 9/1999 | Grollier et al. |
| 6,426,383 B1 | 7/2002 | Fong et al. |
| 6,894,110 B2 | 5/2005 | Fong et al. |
| 7,713,310 B2 | 5/2010 | Lalleman |
| 8,449,871 B2 | 5/2013 | Mougin et al. |
| 2002/0198317 A1 | 12/2002 | Fong et al. |
| 2003/0103923 A1 | 6/2003 | Ohta et al. |
| 2003/0129210 A1 | 7/2003 | Chowdhary |
| 2004/0110650 A1 | 6/2004 | Siddiqui et al. |
| 2004/0247551 A1 | 12/2004 | Yokomaku et al. |
| 2006/0039882 A1 | 2/2006 | Demitz et al. |
| 2006/0067907 A1 | 3/2006 | Mougin et al. |
| 2007/0009472 A1 | 1/2007 | Niebauer et al. |
| 2007/0283977 A1 | 12/2007 | Mougin et al. |
| 2008/0134449 A1 * | 6/2008 | Lalleman ........... 8/408 |
| 2008/0229521 A1 | 9/2008 | Lalleman |
| 2009/0176675 A1 | 7/2009 | Peffly et al. |
| 2010/0147319 A1 | 6/2010 | Lalleman |
| 2010/0147320 A1 | 6/2010 | Lalleman |

FOREIGN PATENT DOCUMENTS

| | | | |
|---|---|---|---|
| EP | 0 122 324 A1 | 10/1984 | |
| EP | 0 239 346 A2 | 9/1987 | |
| EP | 0 337 354 A1 | 10/1989 | |
| EP | 0 530 974 A1 | 3/1993 | |
| EP | 1 051 967 A2 | 11/2000 | |
| EP | 1 568 351 A1 | 8/2005 | |
| EP | 1 776 983 A1 | 4/2007 | |
| EP | 1 923 042 A1 | 5/2008 | |
| EP | 2198837 A1 * | 8/2010 | ............ A61Q 5/00 |
| FR | 1 583 363 | 10/1959 | |
| FR | 1 492 597 | 8/1967 | |
| FR | 2 077 143 | 10/1971 | |
| FR | 2 080 759 | 11/1971 | |
| FR | 2 162 025 | 7/1973 | |
| FR | 2 190 406 | 2/1974 | |
| FR | 2 252 840 | 5/1975 | |
| FR | 2 270 846 | 12/1975 | |
| FR | 2 280 361 | 2/1976 | |
| FR | 2 316 271 A1 | 1/1977 | |
| FR | 2 320 330 | 3/1977 | |
| FR | 2 336 434 | 7/1977 | |
| FR | 2 368 508 | 5/1978 | |
| FR | 2 383 660 | 10/1978 | |
| FR | 2 393 573 | 1/1979 | |
| FR | 2 413 907 | 8/1979 | |
| FR | 2 470 596 | 6/1981 | |
| FR | 2 519 863 | 7/1983 | |
| FR | 2 598 611 A1 | 11/1987 | |
| FR | 2 875 503 A1 | 3/2006 | |
| FR | 2 898 603 A1 | 9/2007 | |
| FR | 2 944 967 A1 | 11/2010 | |
| GB | 1 331 819 | 9/1973 | |
| GB | 1 546 809 | 5/1979 | |
| JP | 2001-220328 A | 8/2001 | |
| JP | 2003-081782 A | 3/2003 | |
| JP | 2003-089620 A | 3/2003 | |
| JP | 2003-095897 A | 4/2003 | |
| WO | 02/49587 A1 | 6/2002 | |
| WO | 03/084487 A1 | 10/2003 | |
| WO | 2007/005577 A2 | 1/2007 | |

* cited by examiner

COMPOSITION COMPRISING A NON-NITROGENOUS ZINC SALT AND A PARTICULAR CATIONIC SURFACTANT

This is a national stage application of PCT/EP2011/073296, filed internationally on Dec. 19, 2011, which claims priority to U.S. Provisional Application No. 61/431,621, filed on Jan. 11, 2011; as well as French Application No. FR 1060954, filed on Dec. 21, 2010, all of which are incorporated herein by reference in their entireties.

The present invention relates to a cosmetic composition comprising at least one particular zinc salt and at least one particular cationic surfactant in a specific weight ratio, and also to the use of such a composition, preferably in the form of a leave-on care product, for conditioning keratin fibres and protecting their artificial colour from fading.

It is known practice to dye the hair with dye compositions comprising oxidation dye precursors, which are generally known as oxidation bases. These oxidation bases are colourless or weakly coloured compounds, which, when combined with oxidizing products, give rise to coloured compounds via a process of oxidative condensation. It is also known that the shades obtained with these oxidation bases can be varied by combining them with couplers or coloration modifiers. The variety of molecules used as oxidation bases and couplers allows a wide range of colours to be obtained.

It is also known practice to dye the hair by direct dyeing. The process conventionally used in direct dyeing consists in applying to the hair direct dyes, which are coloured and colouring molecules that have affinity for the hair, in leaving them to stand on the hair and then in rinsing the fibres.

The colorations resulting therefrom are particularly chromatic colorations but are, however, only temporary or semi-permanent since the nature of the interactions that bind the direct dyes to the keratin fibre and their desorption from the surface and/or the core of the fibre are responsible for their weak dyeing power and their poor fastness with respect to washing.

The artificial colour of the hair afforded by a direct dyeing or oxidation dyeing treatment gradually attenuates on repeated washing and exposure to light, leading over time to fading of the coloration of the hair.

Besides the impairment of the artificial colours, the hair is also damaged due to repeated washing and various dyeing-bleaching treatments. In general, care products such as hair conditioners or leave-on masks or care products are used to make the hair beautiful while affording a good level of treatment. The use of cationic surfactants as conditioning agents in such care products is known.

However, the formulation of zinc salts in such leave-on care products poses numerous difficulties: inter alia, the formulation of zinc salts, especially in the presence of cationic surfactants, leads to compositions that are usually unstable over time and are thus unmarketable.

Thus, there is a need to find cosmetic compositions, especially in the form of a leave-on care product, which can both protect the artificial colour of the hair against the various attacking factors responsible for the fading of the colours (repeated washing, sunlight) and afford the hair a good level of care, and which are stable over time.

The Applicant has discovered, surprisingly, that by formulating cosmetic compositions comprising at least one particular zinc salts and at least one particular cationic surfactant, the drawbacks mentioned above can be overcome, by obtaining compositions that are stable over time, which show satisfactory protection of the artificial colour of the hair against fading of the coloration of the hair, giving the hair good cosmetic properties, and which can be used as leave-on care products.

In particular, the composition according to the invention is stable over time. In particular, it shows satisfactory stability on storage both at room temperature (25° C.) and at higher temperature (for example 37 or 45° C.). This means that the composition of the invention has a texture that changes little or not at all over time and in particular which does not show any syneresis effect over time.

In addition, the composition according to the invention affords more flexible hair, which has a smoother feel and is better coated and shinier.

Thus, one subject of the invention is a cosmetic composition comprising:
  one or more non-nitrogenous zinc salts,
  one or more cationic surfactants defined as follows and
  the weight ratio of the amount of cationic surfactant(s) to the amount of zinc salt(s) being less than or equal to 1.

Another subject of the present invention consists of a cosmetic process for treating keratin fibres, preferably human keratin fibres such as the hair, in which a composition according to the invention is applied to the keratin fibres and the scalp.

Another subject of the present invention concerns the use of a composition according to the invention, preferably in the form of a leave-on care product such as a hair conditioner, for conditioning keratin fibres, preferably human keratin fibres such as the hair, and for protecting their artificial colour from fading.

Other subjects, characteristics, aspects and advantages of the invention will emerge even more clearly on reading the description and the examples that follow.

The composition according to the invention is preferably a leave-on composition, and in particular a composition preferably comprising less than 3% by weight, more preferentially less than 1% by weight and better still no anionic, nonionic, amphoteric or zwitterionic surfactants, relative to the total weight of the composition.

The term "non-nitrogenous zinc salt" means any mineral or organic compound comprising in its structure at least one zinc-based cation and an anion derived from a mineral or organic acid, the said salt not comprising any nitrogen atoms in its structure.

The zinc salt(s) used according to the invention are preferably chosen from water-soluble zinc salts. The term "water-soluble zinc salt" means any salt with a solubility in water of greater than or equal to 0.5% by weight, at a temperature of 25° C.

The zinc salt(s) are chosen from mineral and organic zinc salts, and mixtures thereof.

The term "mineral zinc salt" means any zinc salt possibly containing carbon only in the form of carbonate or hydrogen carbonate ions.

Among the mineral zinc salts that may be used, examples that may be mentioned include zinc sulfate and zinc chloride, and mixtures thereof.

Among the organic zinc salts that may be used, examples that may be mentioned include zinc lactate, zinc gluconate, zinc phenolsulfonate, zinc citrate and zinc salicylate, derivatives thereof, and mixtures thereof.

The zinc salicylate and derivatives thereof according to the invention correspond to the following structure:

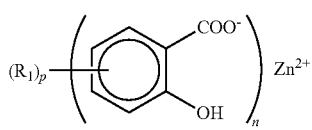

in which:

n=2, p is equal to 0, 1, 2 or 3;

$R_1$ denotes a linear or branched $C_1$-$C_{18}$ alkyl group (for example methyl, ethyl, n-propyl, isopropyl or n-butyl); a linear or branched $C_1$-$C_{18}$ hydroxyalkyl group; a halogen atom (for example iodine, bromine or chlorine); a $C_2$-$C_{18}$ acyl group (for example acetyl); a group $COR_2$ or $OCOR_2$, in which $R_2$ denotes a hydrogen atom or a linear or branched $C_1$-$C_{18}$ alkyl group.

Preferentially, zinc salt(s) are chosen from: zinc sulfate, zinc chloride, zinc lactate, zinc gluconate, zinc salicylate and zinc citrate, and mixtures thereof.

Better still, the zinc salt(s) are chosen from: zinc sulfate, zinc chloride, zinc lactate and zinc gluconate, alone or as a mixture.

Even more preferentially, the zinc salt is an organic zinc salt. Even more preferentially, the zinc salt is zinc lactate or zinc gluconate. Better still, the zinc salt is zinc gluconate.

Zinc gluconate is sold, for example, under the name Givobio G Zn by the company SEPPIC in the composition according to the invention.

The composition according to the invention preferably comprises from 0.1% to 10% by weight and in particular from 0.5% to 6.5% by weight of zinc salt(s) relative to the total weight of the composition.

The concentration of zinc element is preferably less than 2% by weight, in particular ranging from 0.005% to 1.5% by weight and better still from 0.1% to 1% by weight relative to the total weight of the composition.

The composition according to the invention comprises one or more cationic surfactants chosen from the following quaternary ammonium salts:

quaternary ammonium salts of formula (I) below:

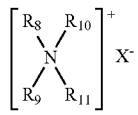

(I)

in which the radicals $R_8$ to $R_{11}$, which may be identical or different, represent an aromatic radical such as aryl or alkylaryl or a linear or branched aliphatic radical comprising from 1 to 30 carbon atoms, at least one of the radicals $R_8$ to $R_{11}$ comprising an alkyl or alkenyl radical comprising from 8 to 30 carbon atoms, preferably from 14 to 30 carbon atoms and better still from 16 to 25 carbon atoms, the aliphatic radicals possibly comprising heteroatoms especially such as oxygen, nitrogen, sulfur and halogens.

The aliphatic radicals are, for example, chosen from alkyl, alkoxy, polyoxy($C_2$-$C_6$)alkylene, alkylamide, ($C_{12}$-$C_{22}$)alkylamido($C_2$-$C_6$)alkyl, ($C_{12}$-$C_{22}$)alkyl acetate or hydroxyalkyl radicals comprising approximately from 1 to 30 carbon atoms, preferably from 14 to 30 and better still from 16 to 25 carbon atoms; $X^-$ is an anion chosen from the group of the halides such a chloride, phosphates, acetates, lactates, ($C_2$-$C_6$)alkyl sulfates, or alkyl- or alkylaryl-sulfonates such as methosulfate;

Among the quaternary ammonium salts of formula (I), it is preferred to use alkyltrimethylammonium chlorides in which the alkyl radical comprises from about 12 to 22 carbon atoms, in particular behenyltrimethylammonium or cetyltrimethylammonium salts or oleocetyldimethylhydroxyethylammonium salts.

quaternary ammonium salts containing at least one ester function, such as those of formula (II) below:

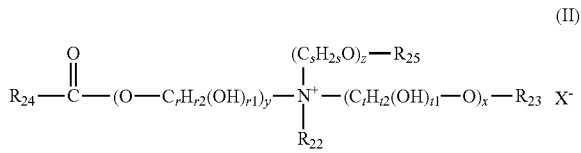

(II)

in which:

$R_{22}$ is chosen from $C_1$-$C_6$ alkyl and $C_1$-$C_6$ hydroxyalkyl or dihydroxyalkyl radicals;

$R_{23}$ is selected from:

the radical

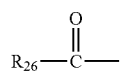

linear or branched, saturated or unsaturated $C_1$-$C_{22}$ hydrocarbon-based radicals $R_{27}$, a hydrogen atom, $R_{25}$ is selected from:

the radical

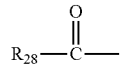

linear or branched, saturated or unsaturated $C_1$-$C_6$ hydrocarbon-based radicals $R_{29}$, a hydrogen atom, $R_{24}$, $R_{26}$ and $R_{28}$, which may be identical or different, are chosen from linear or branched, saturated or unsaturated $C_7$-$C_{21}$ hydrocarbon-based radicals;

r, s and t, which may be identical or different, are integers ranging from 2 to 6;

r1 and t1, which may be identical or different, are equal to 0 or 1, and r2 and t2 are integers such that r2+r1=2r and t1+t2=2t;

y is an integer ranging from 1 to 10;

x and z, which may be identical or different, are integers ranging from 0 to 10;

$X^-$ is a simple or complex, organic or mineral anion;

with the proviso that the sum x+y+z is from 1 to 15, that when x is 0, then $R_{23}$ denotes $R_{27}$ and that when z is 0, then $R_{25}$ denotes $R_{29}$.

The alkyl radicals $R_{22}$ may be linear or branched, but more particularly linear.

$R_{22}$ preferably denotes a methyl, ethyl, hydroxyethyl or dihydroxypropyl radical, and more particularly a methyl or ethyl radical.

Advantageously, the sum x+y+z ranges from 1 to 10.

When $R_{23}$ is a hydrocarbon-based radical $R_{27}$, it may be long and may contain from 12 to 22 carbon atoms, or may be short and may contain from 1 to 3 carbon atoms.

When $R_{23}$ is a hydrocarbon-based radical $R_{27}$, it preferably contains 1 to 3 carbon atoms.

Advantageously, $R_{24}$, $R_{26}$ and $R_{28}$, which may be identical or different, are chosen from linear or branched, saturated or unsaturated $C_{11}$-$C_{21}$ hydrocarbon-based radicals, and more particularly from linear or branched, saturated or unsaturated $C_{11}$-$C_{21}$ alkyl and alkenyl radicals.

Preferably, x and z, which may be identical or different, are equal to 0 or 1.

Advantageously, y is equal to 1.

Preferably, r, s and t, which may be identical or different, are equal to 2 or 3, and even more particularly are equal to 2.

The anion $X^-$ is preferably a halide (chloride, bromide or iodide) or an alkyl sulfate, more particularly methyl sulfate. It is possible, however, to use methanesulfonate, phosphate, nitrate or tosylate, an anion derived from an organic acid, such as acetate or lactate, or any other anion that is compatible with ester-functional ammonium.

The anion $X^-$ is even more particularly chloride or methyl sulfate.

Use is made more particularly, in the composition according to the invention, of the ammonium salts of formula (II) in which:

$R_{22}$ denotes a methyl or ethyl radical;
x and y are equal to 1;
z is equal to 0 or 1;
r, s and t are equal to 2; with r1, r2, t1 and t2 being as defined previously;
$X^-$ being as defined previously;
$R_{23}$ is chosen from:
the radical

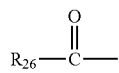

methyl, ethyl or $C_{14}$-$C_{22}$ hydrocarbon-based radicals;
a hydrogen atom;
$R_{25}$ is chosen from:
the radical

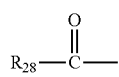

a hydrogen atom;
$R_{24}$, $R_{26}$ and $R_{28}$, which may be identical or different, are selected from linear or branched, saturated or unsaturated $C_{13}$-$C_{17}$ hydrocarbon-based radicals, and preferably from linear or branched, saturated or unsaturated $C_{13}$-$C_{17}$ alkyl and alkenyl radicals.

The hydrocarbon-based radicals are advantageously linear.

Mention may be made, for example, of the compounds of formula (II) such as diacyloxyethyldimethylammonium, diacyloxyethylhydroxyethylmethylammonium, monoacyloxyethyl dihydroxyethylmethylammonium, triacyloxyethylmethylammonium or monoacyloxyethylhydroxyethyldimethylammonium salts (chloride or methyl sulfate, in particular), and mixtures thereof. The acyl radicals preferably contain 14 to 18 carbon atoms and are obtained more particularly from a plant oil such as palm oil or sunflower oil. When the compound contains several acyl radicals, these radicals may be identical or different.

These products are obtained, for example, by direct esterification of triethanolamine, triisopropanolamine, alkyldiethanolamine or alkyldiisopropanolamine, which are optionally oxyalkylenated, with fatty acids or with fatty acid mixtures of plant or animal origin, or by transesterification of the methyl esters thereof. This esterification is followed by a quaternization by means of an alkylating agent such as an alkyl (preferably methyl or ethyl) halide, a dialkyl (preferably methyl or ethyl) sulfate, methyl methanesulfonate, methyl para-toluenesulfonate, glycol chlorohydrin or glycerol chlorohydrin.

Such compounds are sold, for example, under the names Dehyquart® by the company Henkel, Stepanquat® by the company Stepan, Noxamium® by the company Ceca or Rewoquat® WE 18 by the company Rewo-Witco.

It is also possible to use the ammonium salts containing at least one ester function that are described in U.S. Pat. No. 4,874,554 and U.S. Pat. No. 4,137,180.

Use may be made of behenoylhydroxypropyl trimethyl ammonium chloride sold by KAO under the name Quatarmin BTC 131.

Preferably, the ammonium salts containing at least one ester function contain two ester functions.

Among the quaternary ammonium salts containing at least one ester function that may be used, it is preferred to use salts of quaternary ammonium monoesters or of quaternary ammonium diesters, such as dipalmitoylethylhydroxyethylmethylammonium salts.

The cationic surfactants that are particularly preferred in the composition of the invention are chosen from behenyl trimethylammonium chloride, oleocetyldimethylhydroxyethylammonium chloride, cetyltrimethylammonium chloride and dipalmitoylethylhydroxyethylmethylammonium salts.

The cationic surfactant(s) that may be used according to the invention are present in contents ranging from 0.01% to 5% by weight, in particular from 0.02% to 3% by weight and better still from 0.03% to 2% by weight, with respect to the total weight of the composition.

The weight ratio of the amount of cationic surfactant(s) to the amount of zinc salt(s) is less than or equal to 1, preferably from 0.005 to 1 and more preferentially from 0.01 to 1.

The weight ratio of the amount of cationic surfactant(s) to the amount of zinc element is preferably from 0.005 to 10, better still from 0.01 to 10 and better still from 0.1 to 2.

The composition according to the invention may also comprise one or more fatty alcohols.

For the purposes of the present invention, the term "fatty alcohol" means any saturated or unsaturated, linear or branched pure fatty alcohol comprising at least 8 carbon atoms and not comprising any oxyalkylene or glycerol groups.

The fatty alcohol may have the structure R—OH in which R denotes a saturated or unsaturated, linear or branched radical containing from 8 to 40 and preferably from 8 to 30 carbon atoms; R preferably denotes a $C_{12}$-$C_{24}$ alkyl or $C_{12}$-$C_{24}$ alkenyl group. R may be substituted with one or more hydroxyl groups.

Examples of fatty alcohols that may be mentioned include lauryl alcohol, myristyl alcohol, cetyl alcohol, dodecyl alcohol, decyl alcohol, stearyl alcohol, oleyl alcohol, behenyl alcohol, linoleyl alcohol, undecylenyl alcohol, palmitoleyl alcohol, arachidonyl alcohol and erucyl alcohol, and mixtures thereof.

The fatty alcohol may represent a mixture of fatty alcohols, which means that several species of fatty alcohol may coexist, in the form of a mixture, in a commercial product.

Fatty alcohol mixtures that may be mentioned include cetylstearyl alcohol and cetearyl alcohol.

Among all the fatty alcohols that may be used according to the invention, use is preferably made of one or more fatty alcohols chosen from cetyl alcohol, stearyl alcohol and myristyl alcohol.

When they are present, the composition according to the invention preferably comprises from 0.1% to 10% by weight and better still from 1% to 5% by weight of fatty alcohol(s) relative to the total weight of the composition.

The composition according to the invention may also comprise one or more esters of a fatty alcohol and/or of a fatty acid.

As esters of fatty alcohols and/or of fatty acids that may be used, mention may be made of esters derived from the esterification reaction of a fatty alcohol as defined above and/or of a fatty acid as defined below.

For the purposes of the present invention, the term "fatty acid" means any saturated or unsaturated, linear or branched pure carboxylic acid comprising at least 8 carbon atoms and not comprising any oxyalkylene or glycerol groups. Examples of fatty acids that may be mentioned include lauric acid, oleic acid, palmitic acid and stearic acid.

Among all the esters of fatty alcohols and/or of fatty acids that may be used according to the invention, it is preferred to use the cetyl ester or the stearyl ester, and better still a mixture thereof, as sold, for example, under the name Crodamol MS-Pa by the company Croda.

When they are present, the composition according to the invention may preferably comprise from 0.01% to 8% by weight and better still from 0.5% to 5% by weight of fatty alcohol and/or fatty acid ester(s) relative to the total weight of the composition.

The composition according to the invention may also comprise one or more non-silicone cationic polymers.

The cationic polymer(s) that may be used in accordance with the present invention may be selected from all of those already known per se to enhance the cosmetic properties of hair treated with detergent compositions, these being, in particular, the polymers described in patent application EP-A-0 337 354 and in French patent applications FR-A-2 270 846, FR-A-2 383 660, FR-A-2 598 611, FR-A-2 470 596, FR-A-2 519 863 and FR-A-2 875 503.

The preferred cationic polymer(s) are chosen from those that contain in their structure units comprising primary, secondary, tertiary and/or quaternary amine groups that may either form part of the main polymer chain or may be borne by a side substituent directly attached thereto.

Among the cationic polymers that may be mentioned more particularly are polymers of the polyamine, polyaminoamide and polyquaternary ammonium type. Among these polymers, mention may be made of:

(1) Homopolymers or copolymers derived from acrylic or methacrylic esters or amides, cross-linked or not, and comprising at least one of the units of formula (III), (IV), (V) or (VI) below:

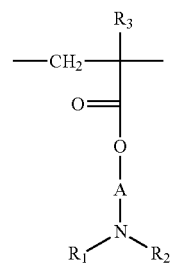

(III)

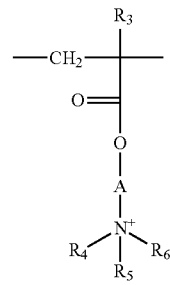

(IV)

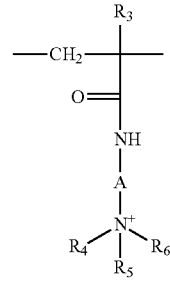

(V)

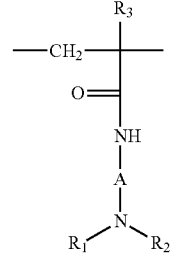

(VI)

in which $R_1$ and $R_2$, which may be identical or different, each represent a hydrogen atom or an alkyl group containing from 1 to 6 carbon atoms, and preferably methyl or ethyl;

$R_3$, which may be identical or different at each occurrence, denotes a hydrogen atom or a $CH_3$ group;

A, which may be identical or different, in each case represents a linear or branched alkyl group of 1 to 6 carbon atoms, preferably 2 or 3 carbon atoms, or a hydroxyalkyl group of 1 to 4 carbon atoms;

$R_4$, $R_5$ and $R_6$, which may be identical or different, each represent an alkyl group containing from 1 to 6 carbon atoms or a benzyl group, and preferably an alkyl group containing from 1 to 6 carbon atoms;

$X^-$ denotes an anion derived from a mineral or organic acid, such as a methosulfate anion or a halide such as chloride or bromide.

The polymers of family (1) can also contain one or more units derived from comonomers which may be chosen from the family of acrylamides, methacrylamides, diacetone acrylamides, acrylamides and methacrylamides substituted on the nitrogen with lower ($C_1$-$C_4$) alkyls, acrylic or methacrylic acids or esters thereof, vinyllactams such as vinylpyrrolidone or vinyl-caprolactam, and vinyl esters.

Thus, among these polymers of family (1), mention may be made of:

copolymers of acrylamide and of dimethylaminoethyl methacrylate quaternized with dimethyl sulfate or with a dimethyl halide, such as the product sold under the name Hercofloc by the company Hercules, copolymers of acrylamide and of methacryloyl-oxyethyl-trimethylammonium chloride which are described, for example, in patent application EP-A-080976 and are sold under the name Bina Quat P 100 by the company Ciba Geigy, the copolymer of acrylamide and of methacryloyl-oxyethyltrimethylammonium methosulfate sold under the name Reten by the company Hercules, quaternized or non-quaternized vinylpyrrolidone/dialkylaminoalkyl acrylate or methacrylate copolymers, such as the products sold under the name Gafquat by the company ISP, such as, for example, Gafquat 734 or Gafquat 755 (Polyquaternium-11), or alternatively the products known as Copolymer 845, 958 and 937. These polymers are described in detail in French patents 2 077 143 and 2 393 573. Polyquaternium-11 is preferably used.

dimethylaminoethyl methacrylate/vinylcaprolactam/vinylpyrrolidone terpolymers, such as the product sold under the name Gaffix VC 713 by the company ISP, vinylpyrrolidone/methacrylamidopropyldimethylamine copolymers sold in particular under the name Styleze CC 10 by ISP, and quaternized vinylpyrrolidone/dimethylaminopropylmethacryl-amide copolymers such as the product sold under the name Gafquat HS 100 by the company ISP, and the crosslinked polymers of methacryloyloxy($C_1$-$C_4$)alkyl tri($C_1$-$C_4$)alkylammonium salts, such as the polymers obtained by homopolymerization of dimethylaminoethyl methacrylate quaternized with methyl chloride, or by copolymerization of acrylamide with dimethylaminoethyl methacrylate quaternized with methyl chloride, the homo- or copolymerization being followed by crosslinking with an olefinically unsaturated compound, more particularly methylene bisacrylamide. A crosslinked acrylamide/methacryloyloxyethyl-trimethylammonium chloride copolymer (20/80 by weight) in the form of a dispersion containing 50% by weight of the said copolymer in mineral oil can be used more particularly. This dispersion is sold under the name Salcare® SC 92 by the company Ciba. Use may also be made of a crosslinked homopolymer of methacryloyloxyethyl trimethylammonium chloride containing approximately 50% by weight of the homopolymer in mineral oil or in a liquid ester. These dispersions are sold under the names Salcare® SC 95 and Salcare® SC 96 by the company Ciba.

(2) Cationic polysaccharides chosen especially from:

a) cellulose ether derivatives comprising quaternary ammonium groups described in French patent 1 492 597, and in particular the polymers sold under the names "JR" (JR 400, JR 125, JR 30M) or "LR" (LR 400, LR 30M) by the company Union Carbide Corporation. These polymers are also defined in the CTFA dictionary as quaternary ammoniums of hydroxyethylcellulose that have reacted with an epoxide substituted with a trimethylammonium group, b) cellulose copolymers or cellulose derivatives grafted with a water-soluble quaternary ammonium monomer, such as hydroxyalkyl celluloses, for instance hydroxymethyl, hydroxyethyl or hydroxypropyl celluloses grafted especially with a methacryloylethyltrimethyl-ammonium, methacrylamidopropyltrimethylammonium or dimethyldiallylammonium salt.

The commercial products corresponding to this definition are more particularly the products, corresponding to the INCI name Polyquaternium-4, sold under the names Celquat L 200 and Celquat H 100 by the company National Starch or Celquat LOR by the company Akzo Nobel.

c) guar gums containing trialkylammonium cationic groups. Use is made, for example, of guar gums modified with a 2,3-epoxypropyltrimethylammonium salt (for example, chloride).

Such products are sold in particular under the trade names Jaguar C13 S, Jaguar C 15, Jaguar C 17 or Jaguar C162 by the company Meyhall.

(3) Polymers formed from piperazinyl units and divalent alkylene or hydroxyalkylene radicals containing straight or branched chains, optionally interrupted with oxygen, sulfur or nitrogen atoms or with aromatic or heterocyclic rings, and also the oxidation and/or quaternization products of these polymers. Such polymers are described, in particular, in French patents 2 162 025 and 2 280 361.

(4) Water-soluble cationic polyaminoamides, prepared in particular by polycondensation of an acid compound with a polyamine; these polyaminoamides may be crosslinked with an epihalohydrin, a diepoxide, a saturated dianhydride, an unsaturated dianhydride, a bis-unsaturated derivative, a bis-halohydrin, a bis-azetidinium, a bis-haloacyldiamine or a bis-alkyl halide or else by an oligomer resulting from the reaction of a bifunctional compound which is reactive towards a bis-halohydrin, a bis-azetidinium, a bis-haloacyldiamine, a bis-alkyl halide, an epihalohydrin, a diepoxide or a bis-unsaturated derivative; these polyaminoamides may be alkylated, or quaternized if they contain one or more tertiary amine functions. Such polymers are described, in particular, in French patents 2 252 840 and 2 368 508.

(5) Polyamino amide derivatives resulting from the condensation of polyalkylene polyamines with polycarboxylic acids followed by alkylation with difunctional agents. Mention may be made, for example, of adipic acid/dialkylamino-hydroxy-alkyldialkylenetriamine polymers in which the alkyl radical comprises from 1 to 4 carbon atoms and preferably denotes methyl, ethyl or propyl. Such polymers are especially described in French patent 1 583 363.

Among these derivatives, mention may be made more particularly of the adipic acid/dimethylaminohydroxy-propyl/diethylenetriamine polymers sold under the name Cartaretine F, F4 or F8 by the company Sandoz.

(6) Polymers obtained by reaction of a polyalkylene polyamine containing two primary amine groups and at least one secondary amine group with a dicarboxylic acid chosen from diglycolic acid and saturated aliphatic dicarboxylic acids having from 3 to 6 carbon atoms. The mole ratio between the polyalkylene polyamine and the dicarboxylic acid is between 0.8:1 and 1.4:1; the polyaminoamide resulting therefrom is reacted with epichlorohydrin in a molar ratio of epichlorohydrin relative to the secondary amine group of the polyaminoamide of between 0.5:1 and 1.8:1. Such polymers are described in particular in U.S. Pat. Nos. 3,227,615 and 2,961,347.

Polymers of this type are sold in particular under the name Hercosett 57 by the company Hercules Inc. or alternatively under the name PD 170 or Delsette 101 by the company Hercules in the case of the adipic acid/epoxypropyl/diethylenetriamine copolymer.

(7) alkyldiallylamine or dialkyldiallylammonium cyclopolymers, such as the homopolymers or copolymers containing, as the main constituent of the chain, units conforming to the formula (VII) or (VIII):

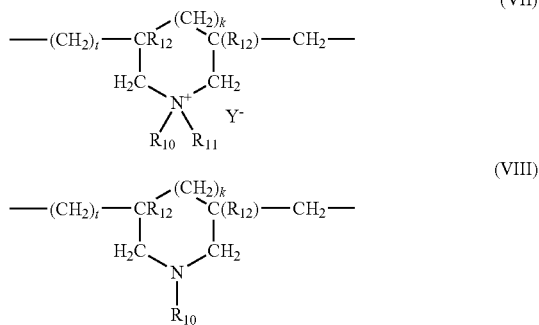

in which formulae: k and t are equal to 0 or 1, the sum k+t being equal to 1; $R_{12}$ denotes a hydrogen atom or a methyl group; $R_{10}$ and $R_{11}$, independently of one another, denote an alkyl group having from 1 to 6 carbon atoms, a hydroxyalkyl group in which the alkyl group has preferably 1 to 5 carbon atoms, a lower ($C_1$-$C_4$) amidoalkyl group, or else $R_{10}$ and $R_{11}$ may, together with the nitrogen atom to which they are attached, denote a heterocyclic group, such as piperidyl or morpholinyl; $Y^-$ is an anion such as bromide, chloride, acetate, borate, citrate, tartrate, bisulfate, bisulfite, sulfate or phosphate. These polymers are especially described in French patent 2 080 759 and in its Certificate of Addition 2 190 406.

$R_{10}$ and $R_{11}$, independently of one another, preferably denote an alkyl group containing from 1 to 4 carbon atoms.

Among the polymers defined above, mention may be made of dialkyldiallylammonium chloride homopolymers, more particularly dimethyldiallylammonium chloride homopolymer (INCI name: Polyquaternium-6) sold, for example, under the name Merquat® 100 by the company Nalco (and homologues thereof of low weight-average molecular masses) and dialkyldiallylammonium chloride homopolymers, more particularly the copolymer of dimethyldiallylammonium chloride and of acrylamide sold under the name Merquat® 550.

(8) the quaternary diammonium polymers containing repeating units corresponding to formula (IX):

in which:

$R_{13}$, $R_{14}$, $R_{15}$ and $R_{16}$, which may be identical or different, represent aliphatic, alicyclic or arylaliphatic groups containing from 1 to 6 carbon atoms or lower ($C_1$-$C_4$) hydroxyaliphatic groups (i.e. the alkyl part of which is $C_1$-$C_4$), or alternatively $R_{13}$, $R_{14}$, $R_{15}$ and $R_{16}$, together or separately, constitute, with the nitrogen atoms to which they are attached, heterocycles optionally containing a second heteroatom other than nitrogen, or alternatively $R_{13}$, $R_{14}$, $R_{15}$ and $R_{16}$ each represent a linear or branched $C_1$-$C_6$ alkyl group substituted with a nitrile, ester, acyl or amide group or a —CO—O—$R_{17}$-E or —CO—NH—$R_{17}$-E group where $R_{17}$ is an alkylene group and E is a quaternary ammonium group;

$A_1$ and $B_1$ represent polymethylene groups containing from 2 to 8 carbon atoms, which may be linear or branched and saturated or unsaturated and may contain, joined to or intercalated in the main chain, one or more aromatic rings, or one or more oxygen or sulfur atoms or sulfoxide, sulfone, disulfide, amino, alkylamino, hydroxyl, quaternary ammonium, ureido, amide or ester groups, and $X^-$ denotes an anion derived from a mineral or organic acid, $A_1$, $R_{13}$ and $R_{15}$ may, with the two nitrogen atoms to which they are attached, form a piperazine ring; moreover, if $A_1$ denotes a linear or branched, saturated or unsaturated alkylene or hydroxyalkylene group, $B_1$ may also denote a group

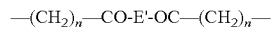

in which n denotes an integer from 0 to 7 and E' denotes:

a) a glycol residue of formula —O—Z—O—, in which Z denotes a linear or branched hydrocarbon group, or a group conforming to one of the following formulae:

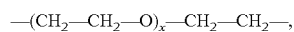

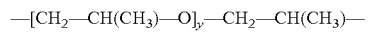

in which x and y each denote an integer from 1 to 4, representing a defined and unique degree of polymerization or any number from 1 to 4 representing an average degree of polymerization, b) a bis-secondary diamine residue such as a piperazine derivative;

c) a bis-primary diamine residue of formula —NH—Y—NH—, in which Y denotes a linear or branched hydrocarbon-based group, or alternatively the divalent group —$CH_2$—$CH_2$—S—S—$CH_2$—$CH_2$—;

d) a ureylene group of formula —NH—CO—NH—.

Preferably, $X^-$ is an anion such as chloride or bromide.

Polymers of this type are described in particular in French patents 2 320 330, 2 270 846, 2 316 271, 2 336 434 and 2 413 907 and U.S. Pat. Nos. 2,273,780, 2,375,853, 2,388,614, 2,454,547, 3,206,462, 2,261,002, 2,271,378, 3,874,870, 4,001,432, 3,929,990, 3,966,904, 4,005,193, 4,025,617, 4,025,627, 4,025,653, 4,026,945 and 4,027,020.

Use may more particularly be made of polymers that are formed from repeating units corresponding to formula (X):

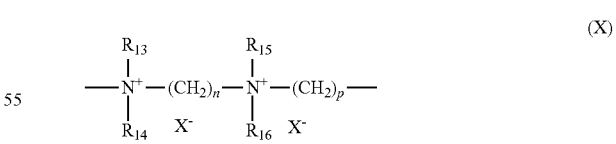

in which $R_{13}$, $R_{14}$, $R_{15}$ and $R_{16}$, which are identical or different, denote an alkyl or hydroxyalkyl group having from 1 to 4 carbon atoms approximately, n and p are integers ranging from 2 to 8 approximately, and $X^-$ is an anion derived from a mineral or organic acid. Preferably, $R_{13}$, $R_{14}$, $R_{15}$ and $R_{16}$ each denote a methyl group. As an example of a polymer that may be used corresponding to formula (X), mention may be made of hexadimethrine chloride, sold under the name Mexomer PO by the company Chimex.

(9) Polyquaternary ammonium polymers composed of units of formula (XI):

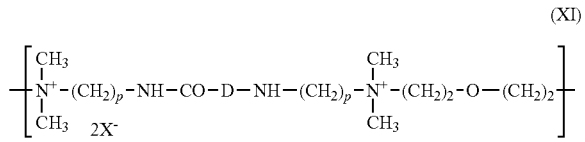

in which:

p denotes an integer ranging from 1 to 6 approximately,

D may be nothing or may represent a group —$(CH_2)_r$—CO— in which r denotes a number equal to 4 or 7, and $X^-$ is an anion derived from a mineral or organic acid.

Cationic polymers comprising units of formula (XI) are especially described in patent application EP-A-122 324 and may be prepared according to the processes described in U.S. Pat. Nos. 4,157,388, 4,390,689, 4,702,906 and 4,719,282.

Among these polymers, the ones that are preferred are those with a molecular mass, measured by carbon-13 NMR, of less than 100 000, and in the formula of which:

p is equal to 3, and a) D represents a group —$(CH_2)_4$—CO—, X denotes a chlorine atom, the molecular mass measured by carbon-13 NMR ($^{13}$C NMR) being about 5600; a polymer of this type is sold by the company Miranol under the name Mirapol-AD1, b) D represents a group —$(CH_2)_7$—CO—, X denotes a chlorine atom, the molecular mass measured by carbon-13 NMR ($^{13}$C NMR) being about 8100; a polymer of this type is sold by the company Miranol under the name Mirapol-AZ1, c) D denotes the value zero, X denotes a chlorine atom, the molecular mass measured by carbon-13 NMR ($^{13}$C NMR) being about 25 500; a polymer of this type is sold by the company Miranol under the name Mirapol-A15, d) a "block copolymer" formed from units corresponding to the polymers described in paragraphs a) and c), sold by the company Miranol under the names Mirapol-9 ($^{13}$C NMR molecular mass of about 7800), Mirapol-175 ($^{13}$C NMR molecular mass of about 8000) and Mirapol-95 ($^{13}$C NMR molecular mass of about 12 500).

Even more particularly, the polymer containing units of formula (XI) in which p is equal to 3, D denotes the value zero and X denotes a chlorine atom, the molecular mass measured by carbon-13 NMR ($^{13}$C NMR) being about 25 500, is preferred according to the invention.

(10) Quaternary polymers of vinylpyrrolidone and of vinylimidazole, for instance the products sold under the names Luviquat FC 905, FC 550 and FC 370 by the company BASF.

(11) Ethoxylated cationic tallow polyamines such as Polyquart H sold by Henkel, referred to under the name polyethylene glycol (15) tallow polyamine in the CTFA dictionary.

(12) vinylamide homopolymers or copolymers and in particular partially hydrolysed vinylamide homopolymers such as poly(vinylamine/vinylamide)s. These polymers are formed from at least one vinylamide monomer corresponding to the following formula:

in which R, $R^1$ and $R^2$ are each chosen from a hydrogen atom, a $C_1$-$C_{20}$ alkyl group, an aryl group and an alkylaryl group in which the alkyl part comprises from 1 to 20 carbon atoms.

In particular, the said monomer may be chosen from N-vinylformamide, N-methyl-N-vinylacetamide and N-vinylacetamide. Preferably, poly(vinylamine/N-vinylformamide) is used, as sold under the name Catiofast VMP by the company BASF or under the name Lupamin 9030 by the company BASF.

These polymers may be formed, for example, by radical polymerization of a vinylamide monomer followed by partial acidic or basic hydrolysis of the amide functions to quaternizable amine functions, as described in patent applications WO 2007/005 577, U.S. Pat. No. 5,374,334, U.S. Pat. No. 6,426,383 and U.S. Pat. No. 6,894,110.

(13) Cationic polyurethanes.

Among the polyurethanes mentioned above, use is preferably made of the polyurethanes formed by the following monomers:

(a1) at least one N-methyldiethanolamine (noted NMDEA), (a2) at least one ethylene/butylene nonionic copolymer as sold under the name Krasol LBH-P 2000, and (b) at least one isophorone diisocyanate (noted IPDI).

Preferably, the amines forming the cationic units (a1) represent from 0.1% to 50%, in particular from 1% to 30% and better still from 5% to 20% by weight relative to the total weight of the final polyurethane.

These polyurethanes and the syntheses thereof are described, for example, in patent application FR-A-2 898 603.

(14) Other cationic polymers that may be used in the context of the invention are cationic proteins or cationic protein hydrolysates, polyalkyleneimines, in particular polyethyleneimines, polymers containing vinylpyridine or vinylpyridinium units, and chitin derivatives.

Among all the cationic polymers that may be used in the context of the present invention, it is preferred to use a copolymer of hydroxyethylcellulose and of diallyldimethylammonium chloride (Polyquaternium-4) or Polyquaternium-11 in the composition according to the invention.

When they are present, the composition according to the invention may comprise from 0.001% to 5% by weight and in particular from 0.01% to 2% by weight of cationic polymer(s) relative to the total weight of the composition.

The composition according to the invention may also comprise one or more silicones, preferably amino silicones.

For the purposes of the present invention, the term "amino silicone" means any silicone comprising at least one primary, secondary or tertiary amine function or a quaternary ammonium group.

The amino silicones used in the cosmetic composition according to the present invention are chosen from:

(a) the compounds corresponding to formula (XII) below:

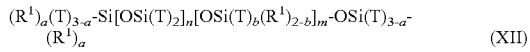

in which:

T is a hydrogen atom or a phenyl, hydroxyl (—OH) or $C_1$-$C_8$ alkyl radical, and preferably methyl, or a $C_1$-$C_8$ alkoxy, preferably methoxy, a denotes the number 0 or an integer from 1 to 3, and preferably 0, b denotes 0 or 1, and in particular 1, m and n are numbers such that the sum (n+m) can range especially from 1 to 2000 and in particular from 50 to 150, it being possible for n to denote a number from 0 to 1999 and in particular from 49 to 149, and for m to denote a number from 1 to 2000 and in particular from 1 to 10;

$R^1$ is a monovalent radical of formula —$C_qH_{2q}L$ in which q is a number from 2 to 8 and L is an optionally quaternized amino group chosen from the following groups:

—N(R²)—CH₂—CH₂—N(R²)₂;

—N(R²)₂; —N⁺(R²); Q⁻;

—N⁺(R²)(H)₂ Q⁻;

—N⁺(R²)₂HQ⁻;

—N(R²)—CH₂—CH₂—N⁺(R²)(H)₂ Q⁻, in which R² denotes a hydrogen atom, a phenyl, a benzyl or a saturated monovalent hydrocarbon-based radical, for example a $C_1$-$C_{20}$ alkyl radical, and Q⁻ represents a halide ion, for instance fluoride, chloride, bromide or iodide.

In particular, the amino silicones corresponding to the definition of formula (XII) are chosen from the compounds corresponding to formula (XIII) below:

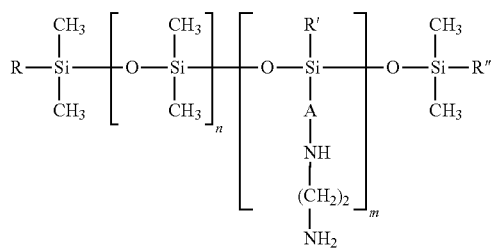

(XIII)

in which R, R' and R", which may be identical or different, denote a $C_1$-$C_4$ alkyl radical, preferably CH₃; a $C_1$-$C_4$ alkoxy radical, preferably methoxy; or OH; A represents a linear or branched, $C_3$-$C_8$ and preferably $C_3$-$C_6$ alkylene radical; m and n are integers dependent on the molecular weight and whose sum is between 1 and 2000.

According to a first possibility, R, R' and R", which may be identical or different, represent a $C_1$-$C_4$ alkyl or hydroxyl radical, A represents a $C_3$ alkylene radical and m and n are such that the weight-average molecular mass of the compound is between 5000 and 500 000 approximately. Compounds of this type are referred to in the CTFA dictionary as "amodimethicones".

According to a second possibility, R, R' and R", which may be identical or different, represent a $C_1$-$C_4$ alkoxy or hydroxyl radical, at least one of the radicals R or R" is an alkoxy radical and A represents a $C_3$ alkylene radical. The hydroxy/alkoxy molar ratio is preferably between 0.2/1 and 0.4/1 and advantageously equal to 0.3/1. Moreover, m and n are such that the weight-average molecular mass of the compound is between 2000 and 10⁶. More particularly, n is between 0 and 999 and m is between 1 and 1000, the sum of n and m being between 1 and 1000.

In this category of compounds, mention may be made, inter alia, of the product Belsil® ADM 652 sold by Wacker.

According to a third possibility, R and R", which are different, represent a $C_1$-$C_4$ alkoxy or hydroxyl radical, at least one of the radicals R or R" is an alkoxy radical, R' represents a methyl radical and A represents a $C_3$ alkylene radical. The hydroxy/alkoxy molar ratio is preferably between 1/0.8 and 1/1.1 and advantageously is equal to 1/0.95. Moreover, m and n are such that the weight-average molecular weight of the compound is between 2000 and 200 000. More particularly, n is between 0 and 1999 and m is between 1 and 1000, the sum of n and m being between 1 and 1000.

More particularly, mention may be made of the product Fluid WR® 1300 sold by Wacker.

According to a fourth possibility, R and R" represent a hydroxyl radical, R' represents a methyl radical and A is a $C_4$-$C_8$ and preferably $C_4$ alkylene radical. Moreover, m and n are such that the weight-average molecular mass of the compound is between 2000 and 10⁶. More particularly, n is between 0 and 1999 and m is between 1 and 2000, the sum of n and m being between 1 and 2000.

A product of this type is especially sold under the name DC 28299 by Dow Corning.

It should be noted that the molecular weight of these silicones is determined by gel permeation chromatography (room temperature, polystyrene standard; μ styragem columns; THF eluent; flow rate of 1 mm/m; 200 μl of a solution containing 0.5% by weight of silicone in THF are injected, and detection is performed by refractometry and UV-metry).

A product corresponding to the definition of formula (XII) is in particular the polymer known in the CTFA dictionary as "trimethylsilyl amodimethicone", corresponding to formula (XIV) below:

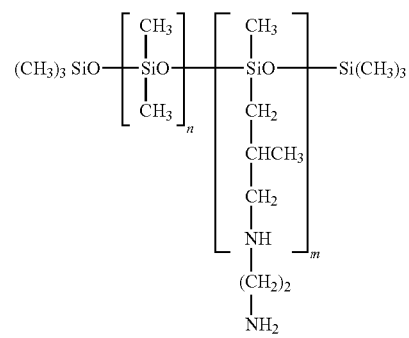

(XIV)

in which n and m have the meanings given above in accordance with formula (XII).

Such compounds are described, for example, in patent EP 95238; a compound of formula (XIV) is sold, for example, under the name Q2-8220 by the company OSI.

(b) the compounds corresponding to formula (XV) below:

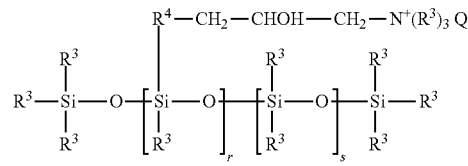

(XV)

in which:

R³ represents a $C_1$-$C_{18}$ monovalent hydrocarbon-based radical, and in particular a $C_1$-$C_{18}$ alkyl or $C_2$-$C_{18}$ alkenyl radical, for example methyl;

R⁴ represents a divalent hydrocarbon-based radical, especially a $C_1$-$C_{18}$ alkylene radical or a divalent $C_1$-$C_{18}$, and for example $C_1$-$C_8$, alkylenoxy radical;

Q⁻ is a halide ion, in particular chloride;

r represents a mean statistical value from 2 to 20 and in particular from 2 to 8;

s represents a mean statistical value from 20 to 200 and in particular from 20 to 50.

Such compounds are described more particularly in U.S. Pat. No. 4,185,087.

A compound falling within this class is the product sold by the company Union Carbide under the name Ucar Silicone ALE 56.

(c) the quaternary ammonium silicones of formula (XVI):

$$R_8-\overset{R_7}{\underset{R_7}{N^+}}-CH_2-\overset{R_7}{\underset{}{CH}}-CH_2-R_6-\left[\overset{R_7}{\underset{R_7}{Si}}-O\right]_r\overset{R_7}{\underset{R_7}{Si}}-R_6-CH_2-CHOH-CH_2-\overset{R_7}{\underset{R_7}{N^+}}-R_8 \quad 2X^-$$

(XVI)

in which:

$R_7$, which may be identical or different, represents a monovalent hydrocarbon-based radical containing from 1 to 18 carbon atoms, and in particular a $C_1$-$C_{18}$ alkyl radical, a $C_2$-$C_{18}$ alkenyl radical or a ring comprising 5 or 6 carbon atoms, for example methyl;

$R_6$ represents a divalent hydrocarbon-based radical, especially a $C_1$-$C_{18}$ alkylene radical or a divalent $C_1$-$C_{18}$, and for example $C_1$-$C_8$, alkylenoxy radical linked to the Si via an SiC bond;

$R_8$, which may be identical or different, represents a hydrogen atom, a monovalent hydrocarbon-based radical containing from 1 to 18 carbon atoms, and in particular a $C_1$-$C_{18}$ alkyl radical, a $C_2$-$C_{18}$ alkenyl radical or a radical —$R_6$—NH-$COR_7$;

$X^-$ is an anion such as a halide ion, especially chloride, or an organic acid salt (acetate, etc.);

r represents a mean statistical value from 2 to 200 and in particular from 5 to 100;

These silicones are described, for example, in patent application EP-A-0 530 974 d) the amino silicones of formula (XVII):

$$\underset{\underset{\underset{NH_2}{|}}{\underset{(C_mH_{2m})}{|}}}{\underset{\underset{NH}{|}}{\underset{(C_nH_{2n})}{|}}}{Si}-\left[O-\left[\overset{R_1}{\underset{R_2}{Si}}-O\right]_x\overset{R_3}{\underset{R_4}{Si}}-R_5\right]_3$$

(XVII)

in which:

$R_1$, $R_2$, $R_3$ and $R_4$, which may be identical or different, denote a $C_1$-$C_4$ alkyl radical or a phenyl group, $R_5$ denotes a $C_1$-$C_4$ alkyl radical or a hydroxyl group, n is an integer ranging from 1 to 5, m is an integer ranging from 1 to 5, and in which x is selected such that the amine number is between 0.01 and 1 meq/g.

The silicone that is particularly preferred is amodimethicone.

When they are present, the composition according to the invention may preferably comprise from 0.01% to 10% by weight and better still from 0.1% to 1.5% by weight of silicone(s) relative to the total weight of the composition.

The composition according to the invention may moreover comprise one or more cosmetic additives commonly used in the art, for instance antioxidants, organic ultraviolet screening agents, inorganic ultraviolet screening agents, thickeners, softeners, antifoams, moisturizers, emollients, plasticizers, mineral fillers, clays, mineral colloids, nacres, fragrances, peptizers, preserving agents, fixing or non-fixing polymers, proteins and vitamins, and mixtures of these compounds.

A person skilled in the art will take care to select the optional additives and the amounts thereof so that they do not interfere with the properties of the compositions of the present invention.

When they are present, these additives may represent an amount ranging from 0.001% to 90% by weight, preferably from 0.001% to 50% by weight and better still from 0.001% to 20% by weight, relative to the total weight of the composition according to the invention.

The composition according to the invention generally comprises water or a mixture of water and one or more organic solvents.

Organic solvents that may be mentioned include lower alcohols ($C_1$-$C_4$), such as ethanol, isopropanol, tert-butanol or n-butanol; polyols such as propylene glycol and glycerol; polyol ethers; $C_5$-$C_{10}$ alkanes; $C_3$-$C_4$ ketones such as acetone; $C_1$-$C_4$ alkyl acetates such as methyl acetate, ethyl acetate and butyl acetate; dimethoxyethane and diethoxyethane; and mixtures thereof.

When the composition according to the invention comprises one or more organic solvents, these solvents may be present in a proportion of from 0.1% to 30% by weight and preferably 0.1% to 10% by weight relative to the total weight of the composition.

The pH of the composition according to the invention, if it is aqueous, generally ranges from 1.5 to 11, preferably from 2 to 6.5 and better still from 2 to 5.

It may be adjusted to the desired value by means of acidifying or basifying agents usually used in the dyeing of keratin fibres, or alternatively using standard buffer systems.

Among the acidifying agents, examples that may be mentioned include mineral or organic acids, for instance hydrochloric acid, orthophosphoric acid, sulfuric acid and sulfonic acids, and carboxylic acids, for instance acetic acid, tartaric acid, citric acid or lactic acid.

Among the basifying agents, examples that may be mentioned include aqueous ammonia, alkali metal carbonates, alkanolamines such as monoethanolamine, diethanolamine and triethanolamine, and also derivatives thereof, sodium hydroxide, potassium hydroxide and the compounds of formula (XVIII) below:

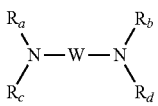 (XVIII)

in which:

W is a propylene residue optionally substituted with a hydroxyl group or a $C_1$-$C_4$ alkyl radical;

$R_a$, $R_b$, $R_c$ and $R_d$, which may be identical or different, represent a hydrogen atom or a $C_1$-$C_4$ alkyl or $C_1$-$C_4$ hydroxyalkyl group.

The composition according to the invention may be in any galenical form normally used for topical application. In particular, the composition according to the invention may be a lotion, a gel, a spray, a mousse or a cream.

The composition according to the invention may be a shampoo, a hair conditioner, a hairsetting product, a dye product, a bleaching product or a permanent-waving product.

Preferably, the composition according to the invention is a hair conditioner.

Another subject of the invention is a cosmetic treatment process that comprises the application to keratin fibres, preferably human keratin fibres such as the hair, and the scalp, of a composition according to the invention as described above, with or without and preferably without subsequent rinsing of the said keratin fibres.

The composition according to the invention that is applied may be massaged on the hair so as to accelerate the penetration, by hand or using any other adequate means, such as a brush or a comb.

The examples which follow are intended to illustrate the invention without, however, being limiting in nature.

EXAMPLES

Compositions According to the Invention

The amounts are indicated as weight percentages of active material (AM) relative to the total weight of each composition.

The weight ratio of the amount of cationic surfactant(s) to the amount of zinc salt(s) (noted R) and the weight ratio of the amount of cationic surfactant(s) to the amount of zinc element(s) (noted R') were calculated for each composition.

| Rinse-out composition 1 | |
|---|---|
| Mixture of cetearyl alcohol/dipalmitoylethylhydroxyethylmethylammonium methosulfate (70/30) (Dehyquart F30 sold by the company Cognis) | 0.6 |
| Zinc gluconate (Givobio G Zn sold by the company SEPPIC) | 5 |
| Water | qs 100 |
| R | 0.04 |
| R' | 0.25 |

| Rinse-out composition 2 | |
|---|---|
| Oleylhydroxyethyldimethylammonium chloride (Chimexane CL sold by the company Chimex) | 0.7 |
| Zinc sulfate heptahydrate (zinc sulfate heptahydrate sold by Merck) | 3 |
| Water | qs 100 |
| R | 0.23 |
| R' | 1 |

| Rinse-out composition 3 | |
|---|---|
| Cetyl alcohol (Lanette 16 sold by the company Cognis) | 3.5 |
| Cetyl/stearyl ester (Crodamol MS-PA sold by the company Croda) | 0.8 |
| Myristyl alcohol (Lanette 14 sold by the company Cognis) | 0.4 |
| Hydroxyethylcellulose (Natrosol 250 HHR sold by the company Aqualon) | 1 |
| Cetyltrimethylammonium chloride (Arquad 16-25 LO sold by the company Akzo Nobel) | 0.6 |
| Behenyltrimethylammonium chloride (Genamin KDMP sold by the company Clariant) | 0.5 |
| Mixture of cetearyl alcohol/dipalmitoylethylhydroxyethylmethylammonium methosulfate (70/30) (Dehyquart F30 sold by the company Cognis) | 0.3 |
| Amodimethicone (Wacker Belsil ADM LOG 1 sold by the company Wacker) | 0.6 |
| Zinc gluconate | 5 |
| Preserving agents | 0.3 |
| Fragrance | 0.4 |
| Water | qs 100 |
| R | 0.24 |
| R' | 1.65 |

| Rinse-out composition 4 | |
|---|---|
| Cetyl alcohol (Lanette 16 sold by the company Cognis) | 3.5 |
| Cetyl/stearyl ester (Crodamol MS-PA sold by the company Croda) | 0.8 |
| Myristyl alcohol (Lanette 14 sold by the company Cognis) | 0.4 |
| Hydroxyethylcellulose (Natrosol 250 HHR sold by the company Aqualon) | 1 |
| Cetyltrimethylammonium chloride (Arquad 16-25 LO sold by the company Akzo Nobel) | 0.6 |
| Amodimethicone (Wacker Belsil ADM LOG 1 sold by the company Wacker) | 0.6 |
| Zinc lactate (zinc lactate sold by the company Lohmann) | 3 |
| Preserving agents | 0.3 |
| Fragrance | 0.4 |
| Water | qs 100 |
| R | 0.2 |
| R' | 0.75 |

| Leave-on composition 5 | |
|---|---|
| Polyquaternium-4 (Celquat LOR sold by the company Akzo Nobel) | 1.5 |
| Cetyltrimethylammonium chloride (Arquad 16-25 LO sold by the company Akzo Nobel) | 0.05 |
| Laureth-4 (Brij L4-LQ-WL sold by the company Croda) | 0.4 |
| Methyl paraben (Nipagin M sold by the company Clariant) | 0.2 |
| Phenoxyethanol (Sepicide LD sold by the company SEPPIC) | 0.5 |

-continued

| Leave-on composition 5 | |
| --- | --- |
| Propylene glycol (Propylene glycol USP/EP sold by the company Dow Chemical) | 2.5 |
| Zinc sulfate heptahydrate (zinc sulfate heptahydrate sold by Merck) | 0.5 |
| Fragrance | 0.3 |
| PEG-40 hydrogenated castor oil (Emulgin HRE 40 sold by the company Cognis) | 0.9 |
| Citric acid | qs pH = 3.2 |
| Water | qs 100 |
| R | 0.1 |
| R' | 0.45 |

| Leave-on composition 6 | |
| --- | --- |
| Polyquaternium-4 (Celquat LOR sold by the company Akzo Nobel) | 0.13 |
| Polyquaternium-11 (Gafquat 755 sold by the company ISP) | 0.03 |
| Amodimethicone (Dow Corning 939 Emulsion sold by the company Dow Corning) | 0.12 |
| Oleylhydroxyethyldimethylammonium chloride (Chimexane CL sold by the company Chimex) | 0.03 |
| Phenoxyethanol (Sepicide LD sold by the company SEPPIC) | 0.7 |
| Caprylyl glycol (Dermosoft Octiol sold by the company Dr Straetmans) | 0.1 |
| Fragrance | 0.2 |
| PEG-40 hydrogenated castor oil (Emulgin HRE 40 sold by the company Cognis) | 0.6 |
| Zinc gluconate (Givobio G Zn sold by the company SEPPIC) | 0.5 |
| Lactic acid (Purac HS 90 sold by the company Purac) | 0.03 |
| Water | qs 100 pH = 5 |
| R | 0.06 |
| R' | 0.42 |

Compositions 1 to 4 according to the invention, applied in the form of rinse-out hair conditioners, give the hair very good smoothness, suppleness and sheen properties.

Compositions 5 and 6 according to the invention, applied in the form of leave-on compositions, give the hair very good smoothness, suppleness and sheen properties.

The invention claimed is:

1. A cosmetic composition comprising:
   at least one non-nitrogenous zinc salt, and
   at least one cationic surfactant chosen from the following quaternary ammonium salts and mixtures thereof:
   quaternary ammonium salts of formula (I):

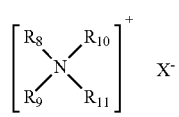

(I)

in which the radicals $R_8$, $R_9$, $R_{10}$, and $R_{11}$, which may be identical or different, are aromatic radicals chosen from aryl radicals, alkylaryl radicals, and linear or branched aliphatic radicals comprising from 1 to 30 carbon atoms, wherein at least one of the radicals $R_8$, $R_9$, $R_{10}$, and $R_{11}$ is chosen from alkyl and alkenyl radicals comprising from 8 to 30 carbon atoms, and wherein the linear or branched aliphatic radicals optionally comprise at least one heteroatom chosen from oxygen, nitrogen, sulfur, and halogen atoms;

quaternary ammonium salts containing at least one ester function, chosen from compounds of formula (II):

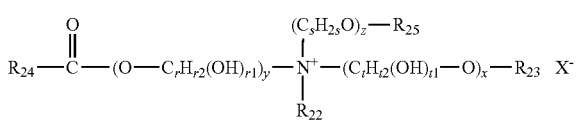

(II)

in which:

$R_{22}$ is chosen from linear or branched $C_1$-$C_6$ alkyl radicals and linear or branched $C_1$-$C_6$ hydroxyalkyl and dihydroxyalkyl radicals;

$R_{23}$ is chosen from:

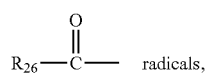

radicals, linear or branched, saturated or unsaturated $C_1$-$C_{22}$ hydrocarbon-based radicals $R_{27}$, and hydrogen, $R_{25}$ is selected from:

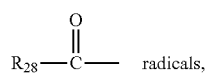

radicals, linear or branched, saturated or unsaturated $C_1$-$C_6$ hydrocarbon-based radicals $R_{29}$, and hydrogen, $R_{24}$, $R_{26}$ and $R_{28}$, which may be identical or different, are chosen from linear or branched, saturated or unsaturated $C_7$-$C_{21}$ hydrocarbon-based radicals;

r, s and t, which may be identical or different, are integers ranging from 2 to 6;

r1 and t1, which may be identical or different, are equal to 0 or 1, r2 and t2 are integers such that r2+r1=2r and t1+t2=2t;

y is an integer ranging from 1 to 10;

x and z, which may be identical or different, are integers ranging from 0 to 10;

$X^-$ is chosen from simple or complex, organic and mineral anions;

with the provisos that the sum x+y+z ranges from 1 to 15, that when x is 0, then $R_{23}$ denotes $R_{27}$ and that when z is 0, then $R_{25}$ denotes $R_{29}$, wherein the weight ratio of the amount of the at least one cationic surfactant to the amount of the at least one zinc salt is less than or equal to 1, and wherein the weight ratio of the amount of the at least one cationic surfactant to the amount of the zinc element ranges from about 0.005 to about 10.

2. A composition according to claim 1, wherein the at least one zinc salt is chosen from water-soluble mineral and organic zinc salts, and mixtures thereof.

3. A composition according to claim 1, wherein the at least one zinc salt is a mineral salt chosen from zinc sulfate and zinc chloride.

4. A composition according to claim 1, wherein the at least one zinc salt is an organic salt chosen from zinc lactate, zinc gluconate, zinc phenolsulfonate, zinc citrate, zinc salicylate, and derivatives thereof corresponding to the following formula, and mixtures thereof:

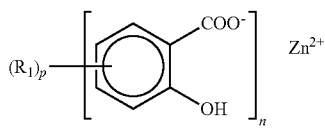

in which:
n is equal to 2, p is equal to 0, 1, 2 or 3; and
$R_1$ is chosen from linear or branched $C_1$-$C_{18}$ alkyl groups; linear or branched $C_1$-$C_{18}$ hydroxyalkyl groups; $C_2$-$C_{18}$ acyl groups; $COR_2$ and $OCOR_2$ groups, in which $R_2$ is chosen from hydrogen and linear or branched $C_1$-$C_{18}$ alkyl groups.

5. A composition according to claim 1, wherein the at least one zinc salt is chosen from zinc lactate and zinc gluconate.

6. A composition according to claim 1, wherein the concentration of the at least one zinc salt ranges from about 0.1% to about 10% by weight relative to the total weight of the composition.

7. A composition according to claim 6, wherein the concentration of the at least one zinc salt ranges from about 0.5% to about 6.5% by weight relative to the total weight of the composition.

8. A composition according to claim 1, wherein the concentration of zinc is less than about 2% by weight relative to the total weight of the composition.

9. A composition according to claim 8, wherein the concentration of zinc ranges from about 0.005% to about 1.5% by weight relative to the total weight of the composition.

10. A composition according to claim 9, wherein the concentration of zinc ranges from about 0.1% to about 1% by weight relative to the total weight of the composition.

11. A composition according to claim 1, wherein the at least one cationic surfactant is chosen from behenyltrimethylammonium chloride, oleocetyldimethylhydroxyethylammonium chloride, cetyltrimethylammonium chloride, and dipalmitoylethylhydroxyethylmethylammonium salt.

12. A composition according to claim 1, wherein the concentration of the at least one cationic surfactant ranges from about 0.01% to about 5% by weight relative to the total weight of the composition.

13. A composition according to claim 12, wherein the concentration of the at least one cationic surfactant ranges from about 0.02% to about 3% by weight relative to the total weight of the composition.

14. A composition according to claim 13, wherein the concentration of the at least one cationic surfactant ranges from about 0.03 to about 2% by weight relative to the total weight of the composition.

15. A composition according to claim 1, further comprising less than about 3% by weight of at least one surfactant chosen from anionic, nonionic, amphoteric, and zwitterionic surfactants, relative to the total weight of the composition.

16. A composition according to claim 1, further comprising at least one additional compound chosen from fatty alcohols, esters of fatty alcohols and fatty acids, non-silicone cationic polymers, and silicones.

17. A composition according to claim 1, wherein the weight ratio of the amount of the at least one cationic surfactant to the amount of the at least one zinc salt ranges from about 0.005 to about 1.

18. A composition according to claim 17, wherein the weight ratio of the amount of the at least one cationic surfactant to the amount of the at least one zinc salt ranges from about 0.01 to about 1.

19. A composition according to claim 1, wherein the composition is a hair conditioner.

20. A cosmetic process for treating keratin fibers, comprising:
(a) applying to the keratin fibers and/or the scalp at least one cosmetic composition comprising:
at least one non-nitrogenous zinc salt, and
at least one cationic surfactant chosen from the following quaternary ammonium salts and mixtures thereof:
quaternary ammonium salts of formula (I):

in which the radicals $R_8$, $R_9$, $R_{10}$, and $R_{11}$, which may be identical or different, are aromatic radicals chosen from aryl radicals, alkylaryl radicals, and linear or branched aliphatic radicals comprising from 1 to 30 carbon atoms, wherein at least one of the radicals $R_8$, $R_9$, $R_{10}$, and $R_{11}$ is chosen from alkyl and alkenyl radicals comprising from 8 to 30 carbon atoms, and wherein the linear or branched aliphatic radicals optionally comprise at least one heteroatom chosen from oxygen, nitrogen, sulfur, and halogen atoms;

quaternary ammonium salts containing at least one ester function, chosen from compounds of formula (II):

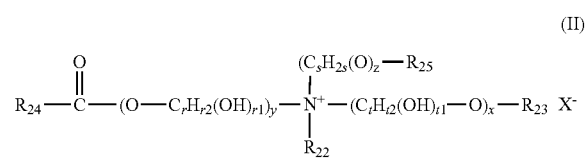

in which:
$R_{22}$ is chosen from linear or branched $C_1$-$C_6$ alkyl radicals and linear or branched $C_1$-$C_6$ hydroxyalkyl and dihydroxyalkyl radicals;
$R_{23}$ is chosen from:

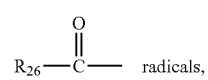 radicals, linear or branched, saturated or unsaturated $C_1$-$C_{22}$ hydrocarbon-based radicals $R_{27}$, and
hydrogen, $R_{25}$ is selected from:

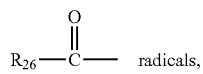

- linear or branched, saturated or unsaturated $C_1$-$C_6$ hydrocarbon-based radicals $R_{29}$, and
- hydrogen, $R_{24}$, $R_{26}$ and $R_{28}$, which may be identical or different, are chosen from linear or branched, saturated or unsaturated $C_7$-$C_{21}$ hydrocarbon-based radicals;

r, s and t, which may be identical or different, are integers ranging from 2 to 6;

r1 and t1, which may be identical or different, are equal to 0 or 1, r2 and t2 are integers such that r2+r1=2r and t1+t2=2t;

y is an integer ranging from 1 to 10;

x and z, which may be identical or different, are integers ranging from 0 to 10;

$X^-$ is chosen from simple or complex, organic and mineral anions;

with the provisos that the sum x+y+z ranges from 1 to 15, that when x is 0, then $R_{23}$ denotes $R_{27}$ and that when z is 0, then $R_{25}$ denotes $R_{29}$, wherein the weight ratio of the amount of the at least one cationic surfactant to the amount of the at least one zinc salt is less than or equal to 1, and (b) optionally rinsing the keratin fibers.

* * * * *